(12) United States Patent
Kunieda (10) Patent No.: US 12,150,804 B2
(45) Date of Patent: Nov. 26, 2024

(54) RADIATION IMAGING APPARATUS, ITS CONTROL METHOD, AND MEDIUM

(71) Applicant: CANON KABUSHIKI KAISHA, Tokyo (JP)

(72) Inventor: Shutaro Kunieda, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 219 days.

(21) Appl. No.: 17/565,536

(22) Filed: Dec. 30, 2021

(65) Prior Publication Data

US 2022/0225956 A1 Jul. 21, 2022

(30) Foreign Application Priority Data

Jan. 15, 2021 (JP) .................................. 2021-005077
Dec. 1, 2021 (JP) .................................. 2021-195715

(51) Int. Cl.
*A61B 6/00* (2024.01)
*A61B 6/42* (2024.01)

(52) U.S. Cl.
CPC .......... *A61B 6/5258* (2013.01); *A61B 6/4233* (2013.01); *A61B 6/542* (2013.01)

(58) Field of Classification Search
CPC ..... A61B 6/5258; A61B 6/4233; A61B 6/542; A61B 6/4283; A61B 6/586
See application file for complete search history.

(56) References Cited

U.S. PATENT DOCUMENTS

| 6,763,084 | B2* | 7/2004 | Boehm | G06T 7/0004 |
| | | | | 348/E5.088 |
| 10,830,910 | B2 | 11/2020 | Ishii | |
| 2004/0252874 | A1* | 12/2004 | Yamazaki | H04N 5/32 |
| | | | | 348/E5.081 |
| 2014/0084175 | A1* | 3/2014 | Ito | G01T 1/24 |
| | | | | 250/370.09 |
| 2015/0153464 | A1* | 6/2015 | Imamura | A61B 6/58 |
| | | | | 378/207 |
| 2019/0257956 | A1 | 8/2019 | Ishii | |

FOREIGN PATENT DOCUMENTS

| JP | 2009-11566 A | 1/2009 |
| JP | 2019-146039 A | 8/2019 |

* cited by examiner

*Primary Examiner* — Christine S. Kim
(74) *Attorney, Agent, or Firm* — VENABLE LLP (57) ABSTRACT

An apparatus appropriately corrects a defective pixel of a radiation image in a radiation imaging apparatus having a function of AEC, both when performing AEC and when not performing AEC, the apparatus selecting a defect map from a first image defect map in which a defective pixel (line), which is a group of defective linear pixels, is not included in a region of interest for detecting the dose of radiation in a pixel region in order to perform an AEC pertaining to stopping of irradiation of radiation, and a second image defect map in which a defective pixel (line) which is a group of defective linear pixels, is included in a region of interest, depending on whether or not an AEC is performed, and corrects the radiation image using the selected defect map.

4 Claims, 8 Drawing Sheets

WITHOUT AEC

FIG. 6B

WITH AEC

RADIATION IMAGING APPARATUS, ITS CONTROL METHOD, AND MEDIUM

BACKGROUND OF THE INVENTION

Field of the Invention

The present disclosure relates to a radiation imaging apparatus for imaging a radiation image based on incident radiation, a control method thereof, and a non-transitory tangible medium having recorded thereon a program for causing a computer to execute the control method.

Description of the Related Art

Radiation imaging apparatuses using radiation detectors that detect radiation such as X-rays are widely used in industries and medical fields. In recent years, multi-functional radiation imaging apparatuses have been investigated, and as one of the functions thereof, a function for monitoring the irradiation of radiation has been considered to be incorporated. This function enables, for example, the detection of the timing at which the irradiation of the radiation from the radiation source is started, the detection of the timing at which the irradiation of the radiation is to be stopped, and the detection of the irradiation amount or the integrated irradiation amount of the radiation. Automatic exposure control (AEC) is also possible by detecting the integrated irradiation amount of radiation transmitted through the subject and stopping the irradiation of radiation by the radiation source when the detected integrated irradiation amount reaches an appropriate amount. In order to realize this automatic exposure control (AEC), for example, a radiation imaging apparatus has been proposed in which pixels for detecting the dose of irradiated radiation are embedded in addition to pixels for photographing a radiation image.

Here, as described in Japanese Patent Application Laid-Open No. 2019-146039, a part of pixels for generating a radiation image may be used for an AEC, and a row in which pixels for use in an AEC are arranged may not be used for generating the radiation image because signals are read out during the AEC. For this reason, in the arrangement shown in Japanese Patent Application Laid-Open No. 2019-146039, a group of linear pixels of rows (lines) which cannot be used for generating a radiation image as a defective line. Further, Japanese Patent Application Laid-Open No. 2009-11566 proposes a method for synthesizing the defect lines described above.

However, in the prior art such as Japanese Patent Application Laid-Open No. 2019-146039, there are points to be improved with respect to correction of missing pixels in a radiation image.

SUMMARY OF THE INVENTION

The present disclosure provides a mechanism for appropriately correcting defective pixels in a radiation image in a radiation imaging apparatus having an automatic exposure control (AEC) function, both in the case of performing AEC and in the case of not performing AEC.

A disclosed aspect of a radiation imaging apparatus for acquiring a radiation image based on incident radiation, comprises a radiation detecting unit including a pixel region provided with a plurality of pixels for detecting the radiation, configured to output an electric signal related to the radiation image; storage unit configured to store (1) a first defect map in which information on the pixel position of a defective pixel among the pixels provided in the pixel region is registered and the defective linear pixel group is not included in a region of interest for detecting the radiation dose in the pixel region in order to perform automatic exposure control for stopping the irradiation of the radiation, and (2) a second defect map in which the defective linear pixel group is included in the region of interest; and a correction unit configured to correct the radiation image by using one of the first defect map and the second defect map selected in accordance with whether or not the automatic exposure control is performed. Other aspect of a radiation imaging apparatus for imaging a radiation image based on incident radiation, comprises: a radiation detecting unit including a pixel region provided with a plurality of pixels for detecting the radiation, configured to output an electric signal related to the radiation image; a storage unit configured to store a defect map in which information relating to the pixel position of a defective pixel among the pixels provided in the pixel region is registered, and in which the defective linear pixel group is not included in a region of interest for detecting the radiation dose in the pixel region in order to perform automatic exposure control for stopping the irradiation of the radiation; a setting unit configured to set the defective linear pixel group in the region of interest; and a correction unit configured to select the validity or invalidity of the setting by the setting unit in accordance with whether or not the automatic exposure control is performed, and correct the radiation image by using the information relating to the selected validity or invalidity and the defect map. In addition, an aspect of the disclosure includes a control method for the radiation imaging apparatus, and a non-transitory tangible medium having recorded thereon a program for causing a computer to execute the control method.

Further features of the present invention will become apparent from the following description of exemplary embodiments with reference to the attached drawings.

DESCRIPTION OF THE PREFERRED EMBODIMENTS

Embodiments are disclosed below with reference to the drawings.

First Embodiment

At the first, a first embodiment is disclosed.

Figure 1:
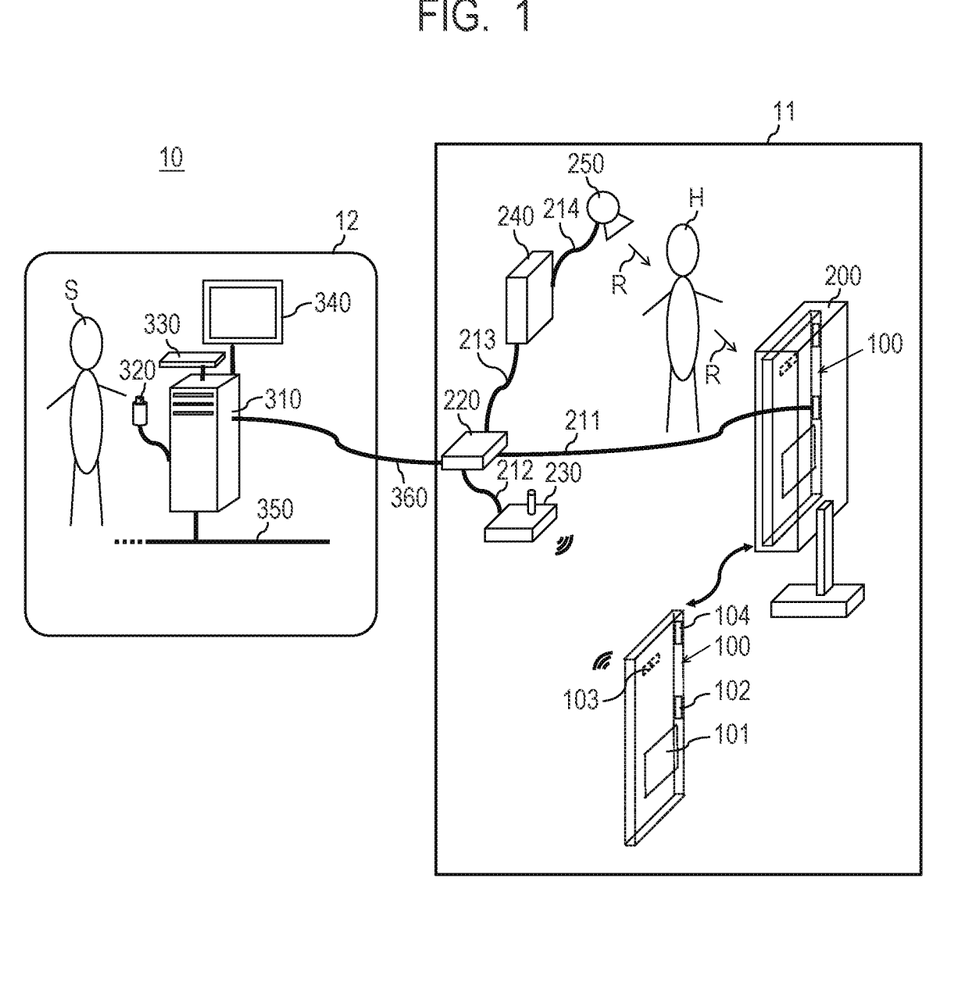
FIG. 1 illustrates an example of a schematic configuration of a radiation imaging system according to a first embodiment of the present disclosure.

FIG. 1 is a diagram showing an example of the schematic configuration of the radiation imaging system 10 according to the first embodiment. As shown in FIG. 1, the radiation imaging system 10 includes a photographing mechanism 11 and a control mechanism 12. A photographing mechanism 11 irradiates the subject H with radiation R and performs radiography of the subject H. In addition to X-rays, the radiation R includes α-rays, β-rays, γ-rays, and various kinds of particle rays.

As shown in FIG. 1, the photographing mechanism 11 includes a radiation imaging apparatus 100, a standing stand 200, a communication cable 211-214, a communication control device 220, an access point (AP) 230, a radiation generating device 240, and a radiation source 250.

As shown in FIG. 1, the control mechanism 12 includes a control device 310, a radiation irradiation switch 320, an input device 330, a display device 340, a local area network (LAN) 350, and a communication cable 360.

Firstly, the respective components inside the photographing mechanism 11 will be described. The radiation imaging apparatus 100 acquires or images a radiation image based on the incident radiation R. In the present embodiment, it is assumed that the radiation imaging apparatus 100 has the above-described automatic exposure control (AEC) function. As shown in FIG. 1, the radiation imaging apparatus 100 includes a power supply control unit 101, a wired communication unit 102, a wireless communication unit 103, and a mounting detection unit 104. The radiation imaging apparatus 100 detects radiation R transmitted through the subject H and generates image data of a radiation image.

The power supply control unit 101 is a component composed of a battery or the like. The wired communication unit 102 communicates information by, for example, a cable connection using a communication standard having a predetermined agreement or a standard such as Ethernet (registered trademark). The wireless communication unit 103 has a circuit board including, for example, an antenna and a communication IC, and the circuit board performs wireless communication processing of a protocol based on a wireless LAN via the antenna. Note that the frequency band, standard and system of the radio communication in the wireless communication unit 103 are not limited, and a system such as proximity radio such as NFC or Bluetooth (registered trademark) or UWB may be used. The wireless communication unit 103 has a plurality of wireless communication systems, and may perform communication by appropriately selecting them. The mounting detection unit 104 is a component for detecting that the radiation imaging apparatus 100 is mounted on the standing stand 200. The mounting detection unit 104 can be realized by providing, for example, a contact type detection element using a limit switch or the like, a detection element such as an inductive type, a capacitive type, or a magnetic proximity sensor, or a signal for electrically detecting when the sensor is mounted on the standing stand 200.

The standing stand 200 is a frame on which the radiation imaging apparatus 100 is mounted and which allows radiation imaging in the standing position. The radiation imaging apparatus 100 can be attached to and detached from the standing stand 200, and can be imaged in either the attached state or the detached state.

The communication cable 211 is a cable for communicably connecting the radiation imaging apparatus 100 and the communication control device 220. The communication cable 212 is a cable for communicably connecting the access point (AP) 230 and the communication control device 220. The communication cable 213 is a cable for communicably connecting the radiation generating device 240 and the communication control device 220. The communication cable 214 is a cable for communicably connecting the radiation source 250 and the radiation generating device 240.

The communication control device 220 is a component for controlling communication in each component of the radiation imaging system 10. Specifically, the communication control device 220 controls, for example, the access point (AP) 230, the radiation generating device 240, and the control device 310 so that they can communicate with each other.

An access point (AP) 230 performs wireless communication with a radiation imaging apparatus 100. For example, the access point (AP) 230 is used to relay communication between the radiation imaging apparatus 100, the control device 310, and the radiation generating device 240 when the radiation imaging apparatus 100 is removed from the standing stand 200 and used. The radiation imaging apparatus 100 or the communication control device 220 may have an access point (AP). In this case, the radiation imaging apparatus 100, the control device 310, and the radiation generating device 240 may communicate with each other via the access point (AP) of the radiation imaging apparatus 100 or the communication control device 220 without via the access point (AP) 230.

The radiation generating device 240 controls the radiation source 250 to irradiate the radiation R based on a predetermined irradiation condition through the communication cable 214. The radiation source 250 is a component for irradiating the subject H with radiation R under the control of the radiation generating device 240.

Next, the components inside the control mechanism 12 will be described. The control device 310 communicates with the radiation generating device 240 and the radiation imaging apparatus 100 via the communication cable 360 and the communication control device 220 to integrally control the radiation imaging system 10.

The radiation irradiation switch 320 is a switch for inputting the irradiation timing of the radiation R from the radiation source 250 by the operation of the operator S.

The input device 330 is a device for inputting an instruction from the operator S, and includes various input devices such as a keyboard and a touch panel.

The display device 340 is a device for displaying an image-processed radiation image or GUI, and includes a display or the like.

The LAN 350 is, for example, a core network in the hospital. The communication cable 360 is a cable for communicably connecting the control device 310 and the communication control device 220.

Figure 2:
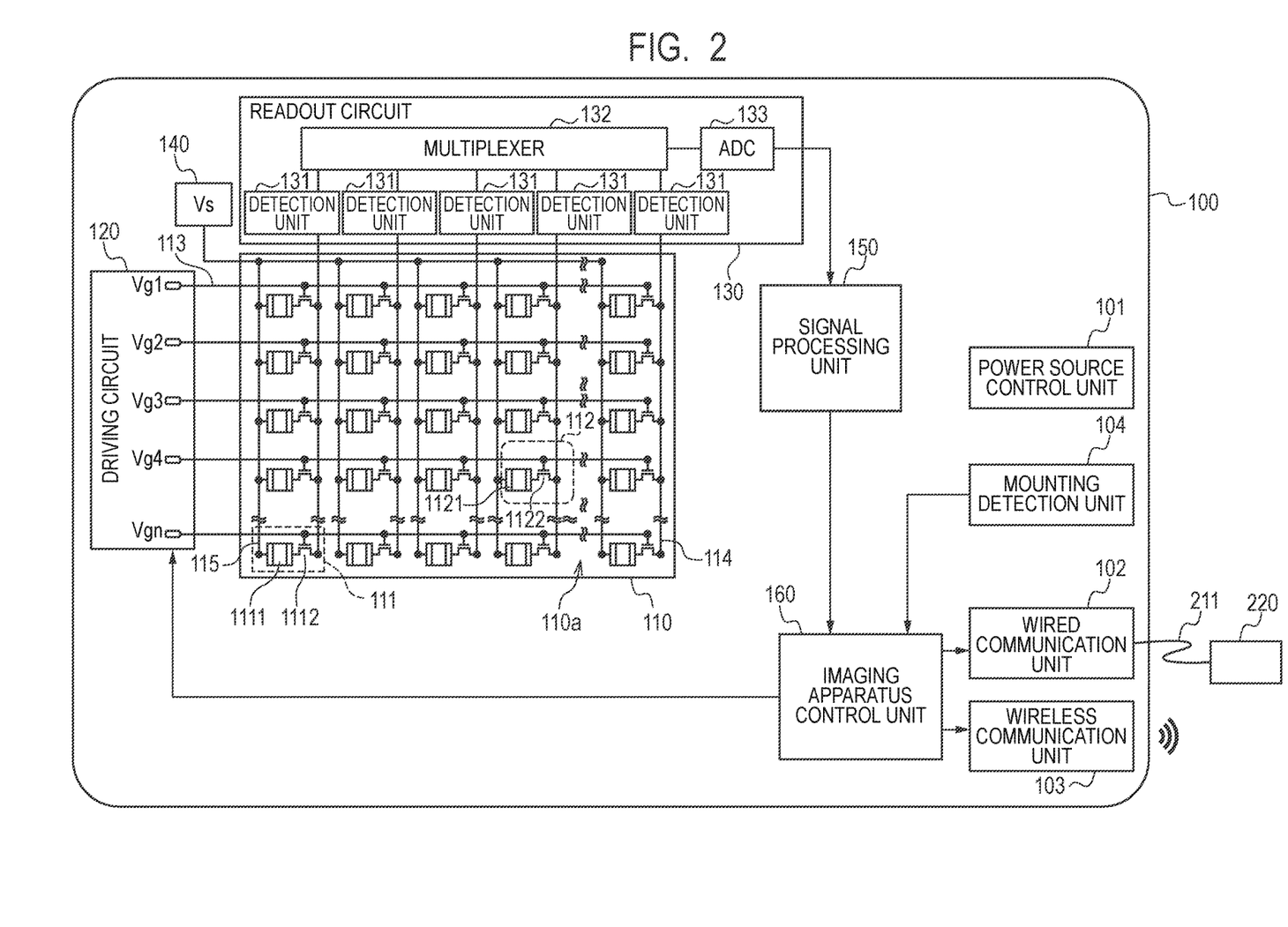
FIG. 2 shows an example of the internal configuration of the radiation imaging device shown in FIG. 1.

Next, the internal configuration of the radiation imaging apparatus 100 shown in FIG. 1 will be described. FIG. 2 is a diagram showing an example of the internal configuration of the radiation imaging apparatus 100 shown in FIG. 1. In FIG. 2, components similar to those shown in FIG. 1 are denoted by the same reference numerals, and a detailed description thereof will be omitted.

As shown in FIG. 1, the radiation imaging apparatus 100 includes a power supply control unit 101, a wired communication unit 102, a wireless communication unit 103, a mounting detection unit 104, a radiation detector 110, a driving circuit 120, a readout circuit 130, a power supply circuit 140, a signal processing unit 150, and an imaging apparatus control unit 160.

The radiation detector 110 includes a pixel region (which may be referred to as an "imaging region") 110a having a plurality of pixels for detecting incident radiation R, and is a component for outputting an electric signal related to a radiation image. Specifically, the pixel region 110a is provided with a plurality of pixels arranged in a matrix. The plurality of pixels provided in the pixel region 110a have a plurality of detection pixels 111 and a plurality of correction pixels 112, and convert incident radiation R into electric signals. Here, the detection pixel 111 is a pixel for generating the radiation image or outputting an electric signal for detecting the dose of the radiation R (the irradiation amount of the radiation R) generated, and the correction pixel 112 is a pixel for outputting an electric signal for removing the dark current component and the crosstalk component.

Each of the plurality of detection pixels 111 includes a conversion element 1111 and a switching element 1112. The conversion element 1111 converts the incident radiation R into an electric signal. The conversion element 1111 includes, for example, a scintillator for converting incident radiation R into light, and a photoelectric conversion element for converting light generated by the scintillator into an electric signal, so as to convert the incident radiation R into an electric signal. In this case, the scintillator is formed in a sheet shape so as to cover the pixel region 110a, and is shared by a plurality of pixels. Note that the conversion element 1111 may be provided with a conversion element for directly converting the incident radiation R into an electric signal without constituting the scintillator described above, so that the incident radiation R is converted into an electric signal. The switching element 1112 is an element for electrically connecting the column signal line 114 and the conversion element 1111, and outputs an electric signal obtained by the conversion element 1111 to the column signal line 114. The switching element 1112 includes, for example, a thin film transistor (TFT) formed of a semiconductor such as amorphous silicon or polycrystalline silicon (preferably polycrystalline silicon) and having an active region.

Each of the plurality of correction pixels 112 includes a conversion element 1121 and a switching element 1122. The conversion element 1121 has the same structure as that of the conversion element 1111, and converts the incident radiation R into an electric signal. The switching element 1122 is formed in the same structure as that of the switching element 1112, and is a switch for electrically connecting the column signal line 114 and the conversion element 1121, and outputs an electric signal obtained by the conversion element 1121 to the column signal line 114.

The correction pixel 112 has the same structure as that of the detection pixel 111. However, the detection pixel 111 has a larger area for detecting the incident radiation R than the correction pixel 112. For example, when the correction pixel 112 has a direct conversion element 1121 for directly converting incident radiation R into an electric signal, the correction pixel 112 adopts a configuration in which a shielding member using heavy metals such as lead is provided on the conversion element 1121 as a shielding member for shielding radiation R. Further, when the correction pixel 112 has, for example, an indirect conversion element 1121 that converts incident radiation R into light by using a scintillator and converts this light into an electric signal, a shielding member that uses, for example, an aluminum shielding film as a shielding member for shielding the light is provided between the conversion element of the correction pixel 112 and the scintillator. The correction pixel 112, whether the conversion element 1121 is a direct type or an indirect type, is arranged in a region where the shielding member overlaps at least a part of the conversion element 1121 of the correction pixel 112 in a plan view with respect to the pixel region 110a.

The correction pixel 112 is shielded from radiation R, detects a dark current component or a crosstalk component, and outputs an electric signal related to the detected dark current component or the crosstalk component. The detection pixel 111 outputs an electric signal related to the radiation image based on the incident radiation R. The signal processing unit 150 generates a more appropriate radiation image by subtracting the electric signal relating to the dark current component or the crosstalk component outputted from the correction pixel 112 from the electric signal relating to the radiation image outputted from the detection pixel 111 via the readout circuit 130.

Figure 3:
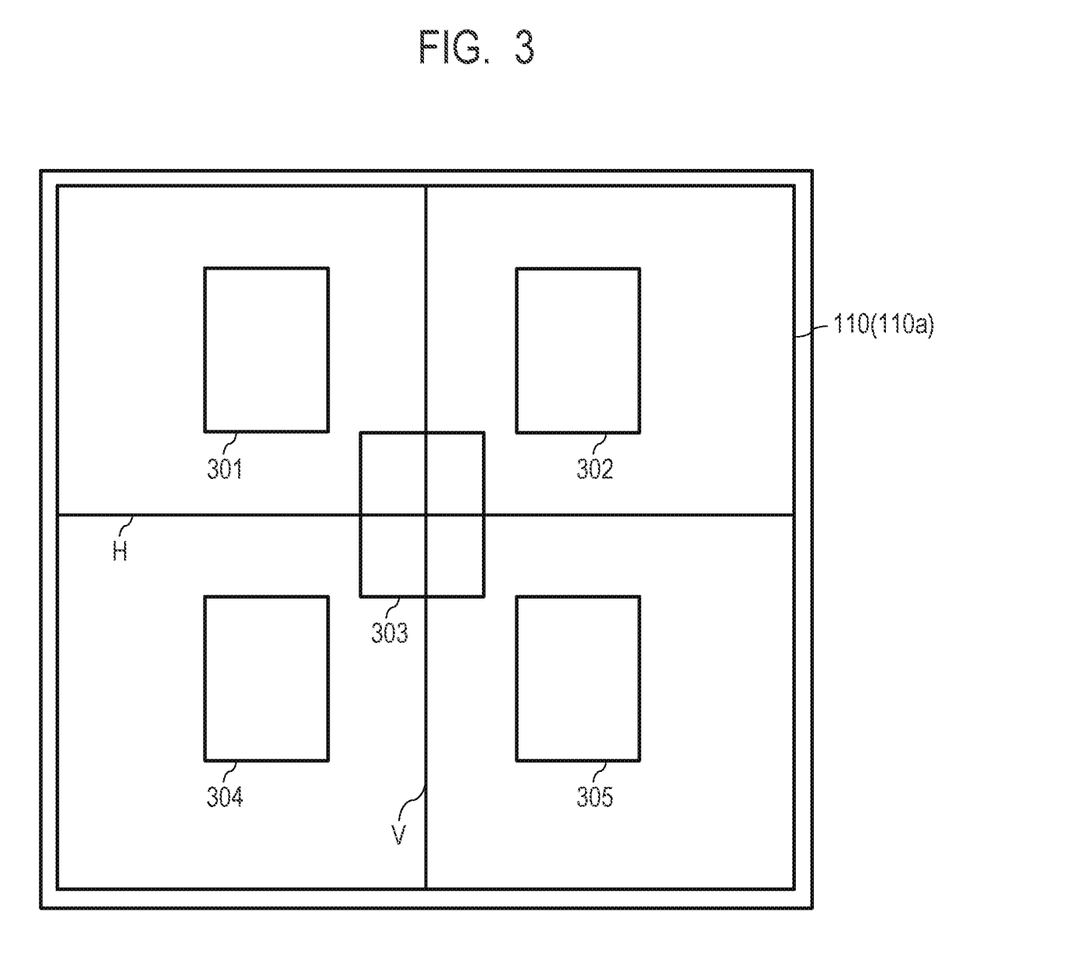
FIG. 3 shows an exemplary arrangement of a plurality of regions of interest (ROI) set within the pixel region of the radiation detector shown in FIG. 2.

FIG. 3 is a diagram showing an arrangement example of a plurality of regions of interest (ROI) 301-305 set in the pixel region 110a of the radiation detector 110 shown in FIG. 2. In the present embodiment, the region of interest (ROI) 301-305 is an area for detecting the dose of the radiation R incident on the pixel region 110a in order to perform the automatic exposure control (AEC) for stopping the irradiation of the radiation R from the radiation source 250. In the present embodiment, in the pixel region 110a of the radiation detector 110, the region of interest 301-305 has a detection pixel 111 and a correction pixel 112, and regions other than the region of interest 301-305 have a detection pixel 111.

Here, the description of FIG. 2 is returned again. The radiation detector 110 further includes a plurality of column signal lines 114, a plurality of driving lines 113, and a plurality of bias lines 115 in the pixel region 110a. The plurality of column signal lines 114 are connected in common to the pixels of each column in the pixel region 110a. The plurality of driving lines 113 are connected in common to the pixels of each row in the pixel region 110a. The plurality of bias lines 115 are connected in common to the pixels of each column in the pixel region 110a.

In the pixel region 110a, the first electrode of the conversion element 1111 of the detection pixel 111 is connected to the first main electrode of the switching element 1112 of the detection pixel 111. The second electrode of the conversion element 1111 of the detection pixel 111 is connected to the bias line 115. Here, one bias line 115 extends in the column direction of the pixel region 110a and is commonly connected to the second electrodes of the plurality of conversion elements 1111 arranged in the column direction. The second main electrode of the switching element 1112 of the detection pixel 111 is connected to the column signal line 114.

In the pixel region 110a, the first electrode of the conversion element 1121 of the correction pixel 112 is connected to the first main electrode of the switching element 1122 of the correction pixel 112. The second electrode of the conversion element 1121 of the correction pixel 112 is connected to the bias line 115. Here, one bias line 115 is commonly connected to the second electrodes of the plurality of conversion elements 1121 arranged in the column direction of the pixel region 110a. The second main electrode of the switching element 1122 of the correction pixel 112 is connected to the column signal line 114.

In this manner, the second main electrodes of both the switching elements 1112 and the switching elements 1122 in each column are respectively connected to the column signal lines 114 in each column. The control electrodes of the switching elements 1112 and the switching elements 1122 in each row are connected to the driving lines 113 in each row. The plurality of column signal lines 114 are connected to the readout circuit 130.

The driving circuit 120 supplies voltages Vg1-Vgn to a plurality of pixels in a row unit through a plurality of driving lines 113.

The power supply circuit 140 supplies a bias voltage Vs to the bias line 115. The power supply control unit 101 includes a battery, a DC-DC converter, and the like. The power supply control unit 101 controls the power supply circuit 140 to generate a power supply voltage for an analog circuit and a power supply voltage for a digital circuit for performing drive control, communication, and the like.

The readout circuit 130 includes a plurality of detection units 131, a multiplexer 132, and an analog-to-digital converter (Hereinafter referred to as "AD converter") 133. As shown in FIG. 2, the plurality of column signal lines 114 are respectively connected to the plurality of detection units 131. At this time, one column signal line 114 is connected to one detection unit 131. The detection unit 131 has, for example, a differential amplifier and amplifies the electric signal of the column signal line 114. The multiplexer 132 selects one of the plurality of detection units 131 in a predetermined order and supplies an electric signal from the selected detection unit 131 to the AD converter 133. The AD converter 133 converts the supplied electric signal from an analog signal to a digital signal and outputs the digital signal.

The signal processing unit 150 processes the electric signal output from the AD converter 133 to output a radiation image based on the radiation R applied to the radiation detector 110 (pixel region 110a) of the radiation imaging apparatus 100. Specifically, the signal processing unit 150 performs signal processing for subtracting the electric signal relating to the dark current component or the crosstalk component generated by the correction pixel 112 from the electric signal relating to the radiation image generated by the detection pixel 111.

The imaging apparatus control unit 160 performs detection of irradiation of the radiation R, calculation of the irradiation amount of the radiation R, calculation of the integrated irradiation amount, and the like on the basis of information from the signal processing unit 150. The imaging apparatus control unit 160 controls the driving circuit 120, the readout circuit 130, and the like on the basis of information from the signal processing unit 150 and a control command from the control device 310 shown in FIG. 1. Further, the imaging apparatus control unit 160 transmits information from the signal processing unit 150 to the control device 310 via the wired communication unit 102 or the wireless communication unit 103.

Figure 4:
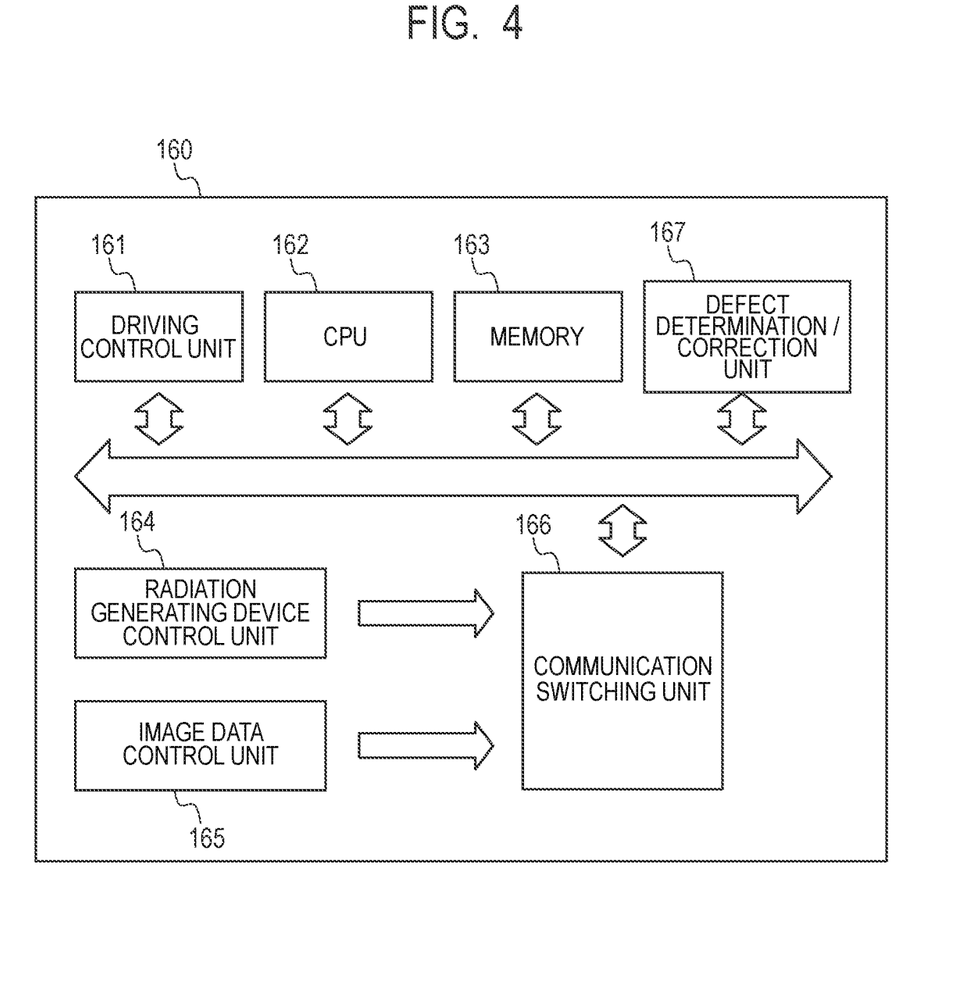
FIG. 4 shows an example of the internal configuration of a control unit of the imaging device shown in FIG. 2.

FIG. 4 is a diagram showing an example of the internal configuration of the imaging apparatus control unit 160 shown in FIG. 2. As shown in FIG. 4, the imaging apparatus control unit 160 includes a driving control unit 161, a CPU 162, a memory 163, a radiation generating apparatus control unit 164, an image data control unit 165, a communication switching unit 166, and a defect determination/correction unit 167.

The driving control unit 161 controls the drive of the driving circuit 120 and the readout circuit 130 shown in FIG. 2 based on the information from the signal processing unit 150 shown in FIG. 2 and the command from the control device 310 shown in FIG. 1.

The CPU 162 controls the entire radiation imaging apparatus 100 using programs and various data stored in the memory 163.

The memory 163 stores, for example, programs to be executed by the CPU 162, and various data. In this case, the various data include various data obtained by the processing of the CPU 162 and image data of the radiation image.

The radiation generating apparatus control unit 164 controls the operation of the radiation generating device 240 shown in FIG. 1 based on the information from the signal processing unit 150 and the information from the driving control unit 161 shown in FIG. 2. The radiation generating apparatus control unit 164 and the radiation generating device 240 communicate information relating to the control of the radiation generating device 240 (for example, notification of the start or stop of irradiation of the radiation R, the amount of irradiation of the radiation R and the integrated amount of irradiation, etc.).

The image data control unit 165 controls the memory 163 to store the image data of the radiation image from the signal processing unit 150 shown in FIG. 2. The image data control unit 165 controls communication with the control device 310 shown in FIG. 1 to communicate image data of the radiation image and information relating to the control (For example, a control command or the like).

The communication switching unit 166 enables communication by the wired communication unit 102 when the communication cable 211 is connected to the radiation imaging apparatus 100, and enables communication by the wireless communication unit 103 when the communication cable 211 is disconnected from the radiation imaging apparatus 100.

Based on the image data of the radiation image stored in the memory 163, the defect determination/correction unit 167 determines whether or not each of the plurality of detection pixels 111 is defective, and generates an image defect map and a dose detection defect map both related to the pixel defect provided in the pixel region 110a. In this case, the defect maps such as the image defect map and the dose detection defect map are those in which information on the pixel position of a defective pixel detected by performing an inspection at the time of shipment inspection after manufacturing or periodic calibration accompanied by irradiation is registered. In the present embodiment, at least two kinds of defect maps are used as the defect maps for images. Specifically, the first image defect map out of the two types of image defect maps is a first image defect map in which a defective linear pixel group is not included in the region of interest 301-305 for detecting the dose of radiation R (the irradiation amount of radiation R) in the pixel region 110a (the linear pixel group for detecting the dose of radiation R is not included as a defective pixel) in order to perform automatic exposure control (AEC) for stopping the irradiation of radiation R from the radiation source 250. The second image defect map out of the two types of image defect maps is a second image defect map in which a defective linear pixel group is included in the region of interest 301-305 (the linear pixel group for detecting the dose of radiation R is included as a defective pixel). The defect determination/ correction unit 167 stores the generated image defect map (including the first image defect map and the second image defect map described above) and the dose detection defect map in the memory 163.

Then, the defect determination/correction unit 167 performs defect determination on the dose of the detected radiation R using the dose detection defect map stored in the memory 163. The defect determination/correction unit 167 performs defect correction on the image data of the radiation image by using the image defect map (including the first image defect map and the second image defect map described above) stored in the memory 163. In this case, in the defect correction, in the case of correcting a point defect (isolated defective pixel), the defect correction is performed by replacing it with the average value of surrounding pixels. In the case of correcting a line defect (defective line) which is a group of defective linear pixels, correction is performed by replacing it with the average value of pixels of the preceding and following orthogonal lines, that is, the average value of the upper and lower pixels. In addition, the line defect, which is a group of defective linear pixels described here, is a group of defective pixels in a row direction, which is a horizontal direction, and the column direction is similarly corrected by substituting the average of the right and left pixels. However, the defect correction is not limited to that described here.

Next, the operation of the radiation imaging system 10 at the time of photographing with the automatic exposure control (AEC) will be described.

The operator S uses the input device 330 to set subject information such as the ID, name, and date of birth of the subject H and photographing information such as the photographing position of the subject H to the control device 310. Subsequently, the operator S uses the input device 330 to input the dose of the radiation R, the maximum irradiation time of the radiation R, the tube current and tube voltage of the radiation source 250, the region of interest for detecting the dose of the radiation R in order to perform the automatic exposure control (AEC), and the site information to the control device 310.

Then, the control device 310 transmits the irradiation conditions of the radiation R inputted from the input device 330, the region of interest for detecting the dose of the radiation R in order to perform the automatic exposure control (AEC), the site information, and the like to the radiation imaging apparatus 100 and the radiation generating device 240.

When the photographing preparation is completed, the operator S depresses the radiation irradiation switch 320. When the radiation irradiation switch 320 is depressed, the radiation source 250 irradiates the subject H with the radiation R under the control of the radiation generating device 240. At this time, the radiation imaging apparatus 100 communicates with the radiation generating device 240 to perform irradiation start control of the radiation R. The radiation R irradiated to the subject H passes through the subject H and enters the radiation imaging apparatus 100 (specifically, radiation detector 110). The radiation imaging apparatus 100 drives a driving line 113 designated for each designated region of interest by a driving circuit 120. The plurality of detection pixels 111 connected to the designated driving line 113 detect the dose of the radiation R (the irradiation amount of the radiation R) and output the detected dose as dose information.

Then, the imaging apparatus control unit 160 calculates an integrated irradiation amount that is an integrated value of the dose of the radiation R detected by the detection pixel 111 during a predetermined period. Further, the imaging apparatus control unit 160 calculates a target value of an appropriate dose from the site information and photographing conditions inputted by the operator S, and determines the irradiation stop timing of the radiation R. When the integrated irradiation amount of the radiation R calculated by the imaging apparatus control unit 160 reaches the target value, the radiation imaging apparatus 100 transmits a radiation irradiation stop signal to the radiation generating device 240 via the communication cable 211, the communication control device 220 and the communication cable 213. In this case, the radiation generating device 240 stops irradiation of the radiation source 250 with the radiation R based on the radiation irradiation stop signal received from the radiation imaging apparatus 100.

After the irradiation of the radiation R is stopped, the detection pixel 111 converts the incident radiation R into an electric signal and generates an electric signal (radiation image signal) relating to the radiation image. An AD converter 133 converts an analog radiation image signal into a digital radiation image signal. Then, the signal processing unit 150 subtracts the electric signal related to the dark current component or the crosstalk component from the radiation image signal output from the AD converter 133 to generate image data of an appropriate radiation image. The imaging apparatus control unit 160 transmits image data of the generated digital radiation image to the control device 310 via the communication cable 211, the communication control device 220, and the communication cable 360.

The control device 310 processes the image data of the radiation image received from the imaging apparatus control unit 160. Then, the control device 310 displays the radiation image based on the image data of the image-processed radiation image on the display device 340. In this embodiment, the control device 310 also functions as an image processing apparatus and a display control apparatus.

Figure 5:
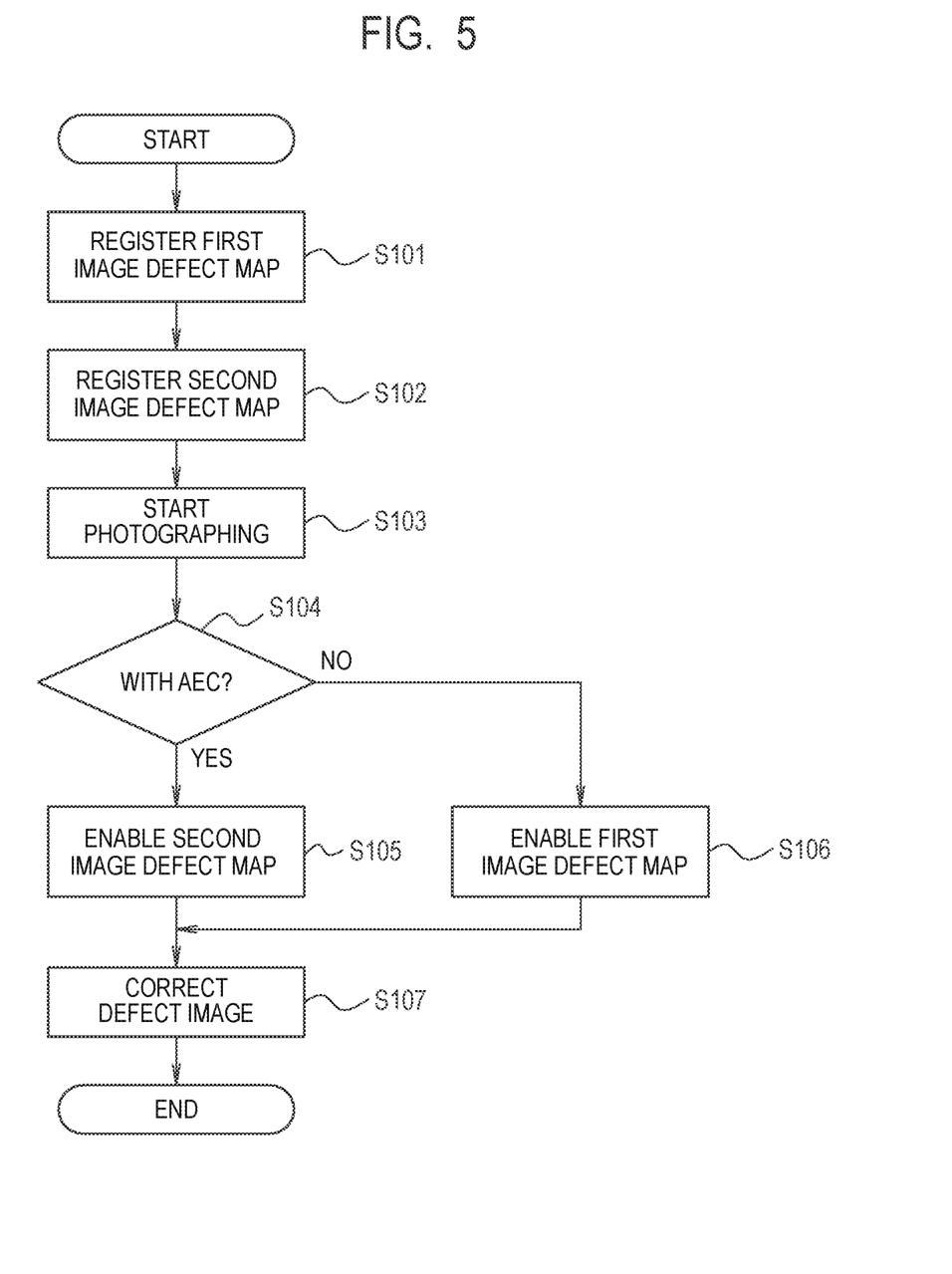
FIG. 5 is a flowchart showing an example of a processing procedure in a control method of a radiation imaging device according to a first embodiment of the present disclosure.

FIG. 5 is a flowchart showing an example of a processing procedure in the control method of the radiation imaging apparatus 100 according to the first embodiment of the present invention. In the processing of the flowchart shown in FIG. 5, processing up to the defective pixel correction of the radiation image is shown.

Before the start of photographing, first, in step S101, the defect determination/correction unit 167 stores and registers the generated first image defect map in the memory 163.

Subsequently, in step S102, the defect determination/correction unit 167 stores and registers the generated second image defect map in the memory 163.

Figure 6A:
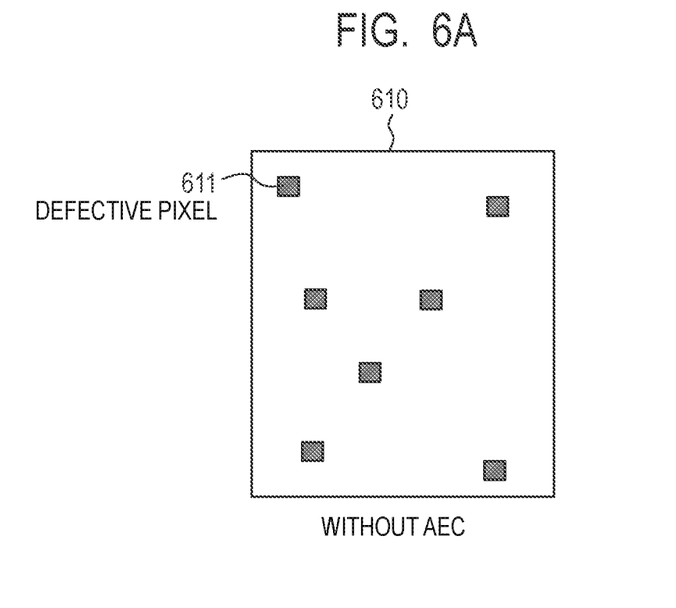
FIGS. 6A and 6B show a first embodiment of the present disclosure and shows specific examples of a first image defect map and a second image defect map stored in the memory shown in FIG. 4.
Figure 6B:
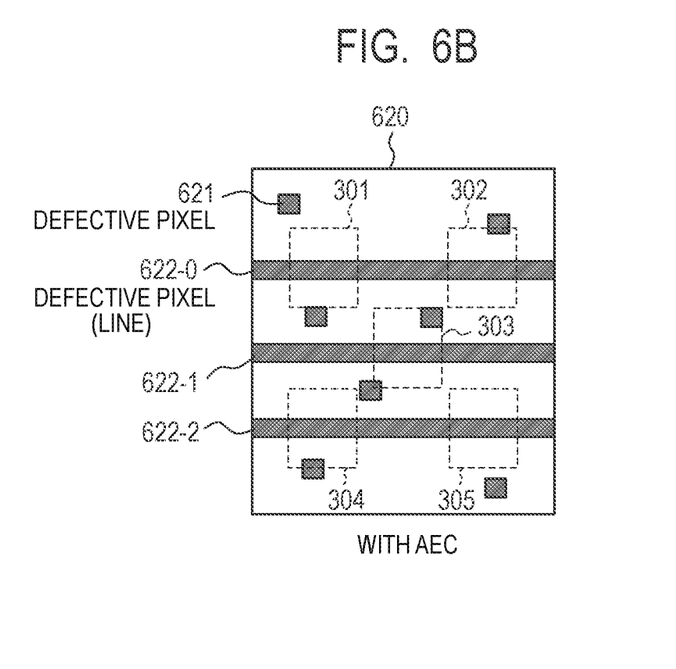

Here, specific examples of the first image defect map registered in step S101 and the second image defect map registered in step S102 will be described. FIGS. 6A and 6B show a first embodiment of the present invention, and shows specific examples of the first image defect map 610 and the second image defect map 620 stored in the memory 163 shown in FIG. 4. Here, the first image defect map 610 shown in FIG. 6A and the second image defect map 620 shown in FIG. 6B are, for example, defect maps related to pixel defects provided in the pixel region 110a of the radiation detector 110 shown in FIG. 3.

The first image defect map 610 shown in FIG. 6A is an image defect map effective when the above-described automatic exposure control (AEC) operation is not performed (That is, in the case where the detection of the dose of the radiation R (the irradiation amount of the radiation R) is not performed in the region of interest 301-305 shown in FIG.

3). The first image defect map 610 shown in FIG. 6A is an image defect map including isolated defective pixels 611 that are point defects.

The second image defect map 620 shown in FIG. 6B is an image defect map effective when the above-described automatic exposure control (AEC) operation is performed (that is, in the case where the detection of the dose of the radiation R (the irradiation amount of the radiation R) is performed in the region of interest 301-305 shown in FIG. 3). The second image defect map 620 shown in FIG. 6B is an image defect map including, in addition to isolated defective pixels 621 that are point defects, defective pixels (lines) 622-0 to 622-2 that are a group of defective linear pixels included in the region of interest 301-305. The pixels included in the region of interest 301-305 may use some of the pixels for generating the radiation image in the AEC operation, and the rows in which the pixels used in the AEC operation are located cannot be used to generate the radiation image because the electrical signals are read out during the AEC operation. Therefore, in this embodiment, in the second image defect map 620 shown in FIG. 6B, the pixel groups of the rows (lines) that cannot be used for generating the radiation image are the defective pixels (lines) 622-0 to 622-2. Here, the second image defect map 620 shown in FIG. 6B is an image defect map in the case where all the region of interest 301-305 are applied as a region of interest for detecting the dose of radiation R in order to perform automatic exposure control (AEC). In the present embodiment, the second image defect map 620 is not limited to the one shown in FIG. 6B, and for example, a second image defect map may be generated for each region of interest used when performing automatic exposure control (AEC), stored in the memory 163, and registered.

On the other hand, since the first image defect map 610 shown in FIG. 6A is an image defect map effective when the automatic exposure control (AEC) operation is not performed, the image defect map does not include the defective pixels (lines) 622-0 to 622-2 shown in FIG. 6B, but only includes the isolated defective pixels 621 that are point defects.

Here, the description of FIG. 5 is returned again. After the processing in step S102 is completed, in step S103, the radiation imaging apparatus 100 starts photographing to acquire a radiation image.

When the photographing is started, in step S104, the imaging apparatus control unit 160 determines whether or not to execute the above-described automatic exposure control (AEC) operation.

As a result of the determination in step S104, when the above-described operation of automatic exposure control (AEC) is performed (S104/YES), the process proceeds to step S105. In step S105, the defect determination/correction unit 167 validates the second image defect map 620 as the image defect map used when the defect image correction of the radiation image obtained by photographing is performed.

On the other hand, as a result of the determination in step S104, if the above-described automatic exposure control (AEC) operation is not performed (step 104/NO), the process proceeds to step S106. In step S106, the defect determination/correction unit 167 validates the first image defect map 610 as the image defect map used when the defect image correction of the radiation image obtained by photographing is performed.

When the process of step S105 is completed or when the process of step S106 is completed, the process proceeds to step S107. In step S107, the defect determination/correction unit 167 corrects the defect image of the radiographic image obtained by photographing by using the valid image defect map (the second image defect map 620 when the AEC operation is performed, and the first image defect map 610 when the AEC operation is not performed).

When the process of step S107 is completed, the process of the flowchart shown in FIG. 5 is completed.

In the radiation imaging apparatus 100 according to the first embodiment described above, the defect determination/correction unit 167 selects either of the first image defect map 610 and the second image defect map 620 according to whether or not automatic exposure control (AEC) is performed, and corrects the radiation image using the selected image defect map. Specifically, the defect determination/correction unit 167 selects the first image defect map 610 to correct the radiation image when not performing AEC, and selects the second image defect map 620 to correct the radiation image when performing AEC. According to this configuration, in the radiation imaging apparatus 100 having the function of automatic exposure control (AEC), the defective pixel correction of the radiation image can be performed appropriately and with high accuracy both in the case of performing AEC and in the case of not performing AEC.

Second Embodiment

Next, a second embodiment of the present invention will be described. In the description of the second embodiment described below, matters common to the first embodiment will be omitted, and matters different from the first embodiment will be described.

The schematic configuration of the radiation imaging system according to the second embodiment is the same as that of the radiation imaging system 10 according to the first embodiment shown in FIG. 1. The internal configuration of the radiation imaging apparatus 100 according to the second embodiment is the same as that of the radiation imaging apparatus 100 according to the first embodiment shown in FIG. 2. The internal configuration of the imaging apparatus control unit 160 according to the second embodiment is the same as that of the imaging apparatus control unit 160 according to the first embodiment shown in FIG. 4.

Figure 7:
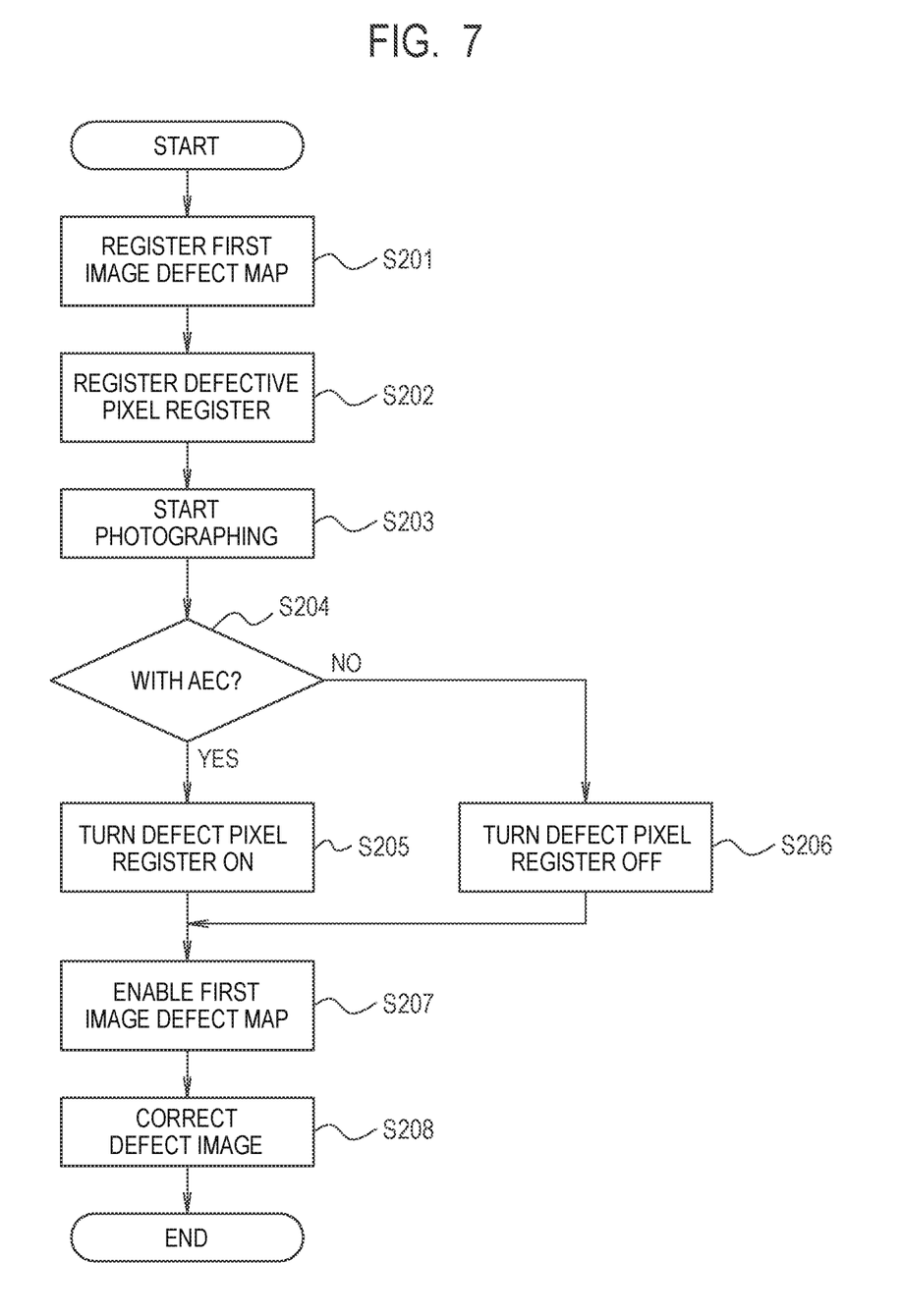
FIG. 7 is a flowchart showing an example of a processing procedure in a control method of a radiation imaging device according to a second embodiment of the present disclosure.

FIG. 7 is a flowchart showing an example of a processing procedure in the control method of the radiation imaging apparatus 100 according to the second embodiment of the present invention. In the processing of the flowchart shown in FIG. 7, processing up to the defective pixel correction of the radiation image is shown.

Before the start of photographing, first, in step S201, the defect determination/correction unit 167 stores and registers the generated first image defect map in the memory 163.

Subsequently, in step S202, in order to perform automatic exposure control (AEC), the defect determination/correction unit 167 sets a defective pixel register related to the defective linear pixel group in a region of interest for detecting the dose of the radiation R in the pixel region 110*a*, and stores and registers it in the memory 163. At this time, as the defective pixel register, information including position information such as coordinates in the defective linear pixel group is set.

Here, specific examples of the first image defect map registered in step S201 and the defect pixel register registered in step S202 will be described. FIGS. 8A to 8D show a second embodiment of the present invention, and shows specific examples of the first image defect map 810 and the defect pixel register stored in the memory 163 shown in FIG. 4.

Figure 8A:
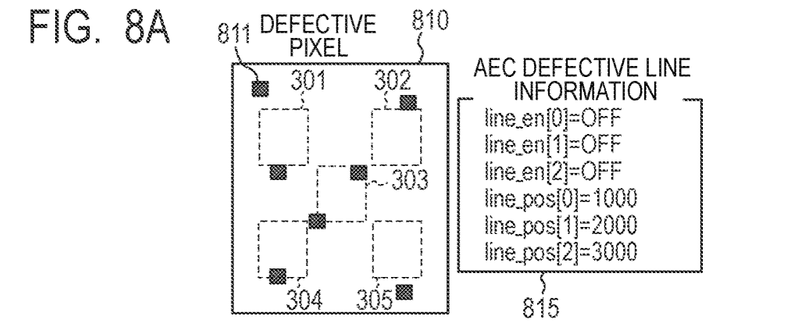
FIGS. 8A, 8B, 8C and 8D show a second embodiment of the present disclosure, showing specific examples of a first image defect map and a missing pixel register stored in the memory shown in FIG. 4.
Figure 8B:
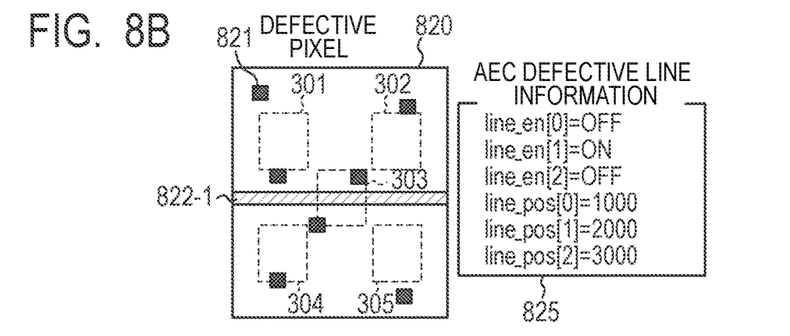
Figure 8C:
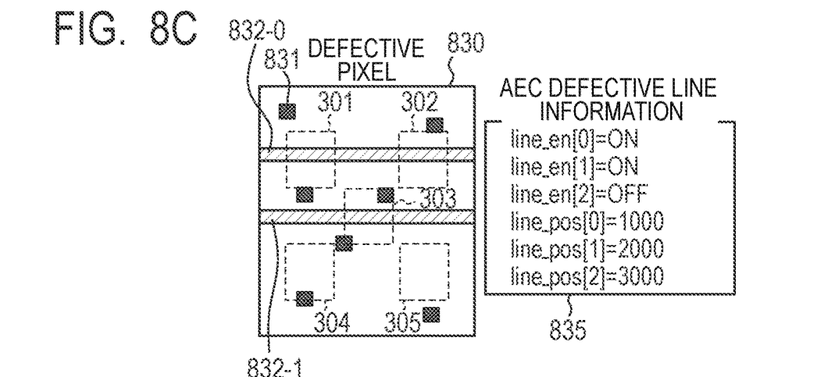
Figure 8D:
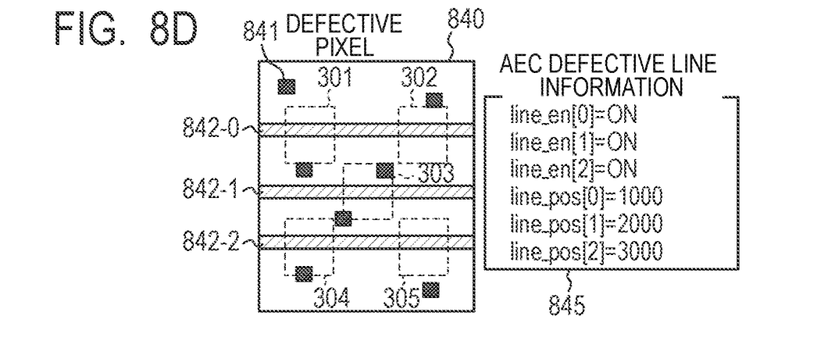

The image defect maps shown in FIGS. 8A to 8D are common in that they include isolated defective pixels (defective pixel 811 in FIG. 8A, defective pixel 821 in FIG. 8B, defective pixel 831 in FIG. 8C, and defective pixel 841 in FIG. 8D that are point defects). In the image defect map shown in FIGS. 8B to 8D, a defective pixel register for a defective pixel (line), which is a group of defective linear pixels, is registered in accordance with a region of interest for detecting the dose of radiation R related to automatic exposure control (AEC). In the AEC defect line information 815-845 corresponding to the image defect maps shown in FIGS. 8A to 8D, the positions line_pos [0] to line_pos [2] of the defect lines are common, but the defect line enable lines line_en [0] to line_en [2] indicating whether or not each defect line is effective are different.

The image defect map 810 shown in FIG. 8A is a first image defect map that is set when the automatic exposure control (AEC) operation is not performed (that is, in the case where the detection of the dose of the radiation R (the irradiation amount of the radiation R) is not performed in the region of interest 301-305 shown in FIG. 3). The image defect map (first image defect map) 810 shown in FIG. 8A is an image defect map including only isolated defect pixels 811 that are point defects. In the image defect map (first image defect map) 810 shown in FIG. 8A, as shown in the AEC defect line information 815, all of the defect line enable lines_en [0] to line_en [2] are OFF.

The image defect map 820 shown in FIG. 8B shows a state set when the automatic exposure control (AEC) operation is performed. Specifically, the image defect map 820 shown in FIG. 8B is an image defect map in which a defect pixel register related to a defective pixel (line) 822-1, which is a group of defective linear pixels, is registered at a position of a central region of interest 303 in an image defect map (first image defect map) 810 shown in FIG. 8A, for detecting a dose of radiation R related to automatic exposure control (AEC). In the image defect map 820 shown in FIG. 8B, as shown in the AEC defect line information 825, only the defect line enable line_en [1] is turned on.

The image defect map 830 shown in FIG. 8C shows a state set when the automatic exposure control (AEC) operation is performed. Specifically, the image defect map 830 shown in FIG. 8C is an image defect map in which a defect pixel register related to the defective pixels (lines) 832-0 to 832-1, which are a group of defective linear pixels, is registered at the position of the region of interest 301-303 in an image defect map (first image defect map) 810 shown in FIG. 8A, in the lung field for detecting the dose of the radiation R related to the automatic exposure control (AEC). In the image defect map 830 shown in FIG. 8C, as shown in the AEC defect line information 835, only the defect line enable line_en [2] is OFF.

The image defect map 840 shown in FIG. 8D shows a state set when the automatic exposure control (AEC) operation is performed. Specifically, the image defect map 840 shown in FIG. 8D is an image defect map in which the defect pixel register related to the defective pixels (lines) 842-0 to 842-2, which are a group of defective linear pixels, is registered at the positions of all the regions of interest 301-305 in an image defect map (first image defect map) 810 shown in FIG. 8A, for detecting the dose of the radiation R related to the automatic exposure control (AEC). In the image defect map 840 shown in FIG. 8D, as shown in the AEC defect line information 845, the defect line enable line_en [0] to line_en [2] are all turned ON.

Here, the description of FIG. 7 is returned again. After the processing in step S202 is completed, in step S203, the radiation imaging apparatus 100 starts photographing to acquire a radiation image.

When the photographing is started, in step S204, the imaging apparatus control unit 160 determines whether or not to execute the above-described automatic exposure control (AEC) operation.

As a result of the determination in step S204, when the above-described operation of the automatic exposure control (AEC) is performed (S204/YES), the process proceeds to step S205. In step S205, the defect determination/correction unit 167 makes the defective pixel register registered in step S202 valid (turns on the defective pixel register).

On the other hand, as a result of the determination in step S204, if the above-described operation of the automatic exposure control (AEC) is not performed (step 204/NO), the process proceeds to step S206. In step S206, the defect determination/correction unit 167 invalidates the defective pixel register registered in step S202 (turns off the defective pixel register).

When the process of step S205 is completed or when the process of step S206 is completed, the process proceeds to step S207. In step S207, the defect determination/correction unit 167 validates the first image defect map registered in step S201. Here, if the above-described automatic exposure control (AEC) operation is not performed, the state of the defect map for image used in a case where the defect pixel correction of the radiation image is performed is the state of the image defect map 810 shown in FIG. 8A. In addition, when the above-described automatic exposure control (AEC) operation is performed, the state of the defect map for image used in a case where the defect pixel correction of the radiation image is performed is one of the states of the image defect maps 820-840 shown in FIGS. 8B to 8D, depending on the region of interest for detecting the dose of the radiation R related to the AEC.

Subsequently, in step S208, the defect determination/correction unit 167 corrects the defect image of the radiographic image obtained by the photographing by using the first image defect map valid in step S207 and the information of the defect pixel register (information on the defective pixel register that became valid in step S205 or information on the defective pixel register that became invalid in step S206).

When the process of step S208 is completed, the process of the flowchart shown in FIG. 7 is completed.

In the radiation imaging apparatus 100 according to the second embodiment described above, the defect determination/correction unit 167 sets a group of defective linear pixels in the region of interest of the pixel region 110a, selects whether the setting is valid or invalid according to whether or not automatic exposure control (AEC) is performed, and corrects the radiation image by using the selected valid or invalid information and the first image defect map 810. Specifically, the defect determination/correction unit 167 selects invalidity of the setting when not performing AEC, corrects the radiation image by using the information related to the selected invalidity and the first image defect map 810, selects the validity of the setting when performing AEC, and corrects the radiation image by using the selected information related to the validity and the first image defect map 810. According to this configuration, in the radiation imaging apparatus 100 having the function of automatic exposure control (AEC), the defective pixel correction of the radiation image can be performed appropriately and with high accuracy both in the case of performing AEC and in the case of not performing AEC.

Other Embodiments

In the first and second embodiments described above, defect determination is performed from a radiation image obtained by irradiating radiation R, but defect determination may be performed using an image obtained without irradiating radiation R. In the first and second embodiments described above, defect determination/correction is performed from one type of image, but defect determination/correction may be performed for images in a plurality of photographing modes (for example, a size difference due to binning processing, a sensor gain difference, a fluoroscopic mode, a continuous photographing mode, etc.). In the first and second embodiments described above, in the operation of automatic exposure control (AEC), defective pixels as a linear pixel group have been described as an example, but the present invention is applicable not only to the case where the defective pixels are linearly located, but also to various defective pixel shapes. For example, by specifying a pixel to be used for the operation of automatic exposure control (AEC) among the detection pixels 111 and connecting the pixel to a separately provided AEC dedicated driving line, it is possible to discretely position defective pixels accompanying the AEC operation. In this case, the defect map corresponding to the layout of the pixels connected to the AEC exclusive driving line is generated, and the defect pixel correction is performed by using the defect map. In the first and second embodiments described above, the pixels used for the automatic exposure control (AEC) are arranged in the region of interest (ROI) 301-305 shown in FIG. 3, but the pixels used for the AEC need not be limited to the pixels located in the ROI. In this manner, the present invention provides a mechanism for properly correcting defective pixels in a radiation image in accordance with whether or not an AEC operation using pixels located in various locations in various layouts is performed.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

It should be noted that the foregoing embodiments are merely illustrative examples of the embodiments of the present invention, and the technical scope of the present invention should not be interpreted in a limited manner. That is, the present invention is not limited to the embodiments described above, and various modifications and variations are possible without departing from the spirit and scope of the present invention. Accordingly, in order to make the scope of the present invention public, the following claims are attached.

According to the present invention, in the radiation imaging apparatus having the function of automatic exposure control (AEC), the defective pixel correction of the radiation image can be appropriately performed both in the case of performing AEC and in the case of not performing AEC.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-005077, filed Jan. 15, 2021, and Japanese Patent Application No. 2021-195715, filed Dec. 1, 2021, which are hereby incorporated by reference herein in their entirety.

What is claimed is:

1. A method for controlling a radiation imaging apparatus that acquires a radiation image based on incident radiation, comprising a radiation detecting unit including a pixel region provided with a plurality of pixels for detecting the radiation, the radiation detecting unit outputting an electrical signal relating to the radiation image, the method comprising the steps of:
a storage step of storing a first defect map in which information on a pixel position of a defective pixel among the pixels provided in the pixel region is registered, and in which a defective linear pixel group is not included in a region of interest for detecting a radiation dose in the pixel region in order to perform automatic exposure control for stopping the irradiation of the radiation, and a second defect map in which information on the pixel position of a defective pixel among the pixels provided in the pixel region is registered, and in which the defective linear pixel group is included in the region of interest; and
a correcting step of correcting the radiation image by using one of the first defect map and the second defect map selected in accordance with whether or not the automatic exposure control is performed.

2. A non-transitory tangible medium having recorded thereon a program for causing a computer to execute steps of the method according to claim 1.

3. A method for controlling a radiation imaging apparatus that acquires a radiation image based on incident radiation, comprising: a radiation detecting unit including a pixel region provided with a plurality of pixels for detecting the radiation, the radiation detecting unit outputting an electrical signal relating to the radiation image, the method comprising the steps of:
a storage step of storing a defect map in which information relating to the pixel position of a defective pixel among the pixels provided in a pixel region is registered, and in which a defective linear pixel group is not included in a region of interest for detecting a radiation dose in the pixel region in order to perform automatic exposure control for stopping the irradiation of the radiation;

a setting step of setting the defective linear pixel group in the region of interest; and a correction step of selecting a validity or invalidity of the setting by the setting step in accordance with whether or not the automatic exposure control is performed, and correcting the radiation image by using the information relating to the selected validity or invalidity and the defect map.

4. A non-transitory tangible medium having recorded thereon a program for causing a computer to execute steps of the method according to claim 3.

* * * * *